United States Patent [19]

Reist et al.

[11] Patent Number: 5,532,225
[45] Date of Patent: Jul. 2, 1996

[54] ACYCLIC PURINE PHOSPHONATE NUCLEOTIDE ANALOGS AS ANTIVIRAL AGENTS, AND RELATED SYNTHETIC METHODS

[75] Inventors: Elmer J. Reist, Menlo Park; Beatrice Ruhland-Fritsch; Pricilla A. Sturm, both of Mountain View, all of Calif.

[73] Assignee: SRI International, Menlo Park, Calif.

[21] Appl. No.: 922,937

[22] Filed: Jul. 31, 1992

[51] Int. Cl.[6] .................. A61K 31/675; C07F 9/6512
[52] U.S. Cl. .................. 514/81; 544/244; 549/555; 558/187; 558/189
[58] Field of Search .................. 544/244; 514/81

[56] References Cited

U.S. PATENT DOCUMENTS

| | | | |
|---|---|---|---|
| 3,238,191 | 3/1966 | Myers | 536/126.2 |
| 3,625,982 | 12/1971 | Christensen et al. | 544/244 |
| 3,662,031 | 5/1972 | Moffatt | 558/83 |
| 4,910,307 | 3/1990 | Wyatt | 544/244 |
| 5,047,533 | 9/1991 | Reist et al. | 544/244 |
| 5,166,198 | 11/1992 | Harnden et al. | 544/244 |

FOREIGN PATENT DOCUMENTS

| | | |
|---|---|---|
| 49072 | 4/1982 | European Pat. Off. |
| 74306 | 3/1983 | European Pat. Off. |
| 173624 | 3/1986 | European Pat. Off. |
| 1243231 | 8/1971 | United Kingdom. |
| 8805438 | 7/1988 | WIPO. |

OTHER PUBLICATIONS

*Advanced Organic Chemistry* (4th. Ed.) by Jerry March, pp. 120–121 (1992).
*Stereo Chemistry of Carbon Compounds* by Ernest L. Eliel pp. 47–56 (1962).
Prisbe et al., *J. Med. Chem.* 29:671,675 (1986).
Striecher et al., *Chemica Scripta* 26:179–182 (1986).
Duke et al., *Antiviral Research* 6:299–308 (1986).

*Primary Examiner*—Emily Bernhardt
*Attorney, Agent, or Firm*—Reed & Robins

[57] ABSTRACT

Acyclic purine phosphonate nucleotide analogs useful to treat herpes viral infections are provided in enantiomerically pure form. These antiviral agents have the structural formula (Ia) or (Ib)

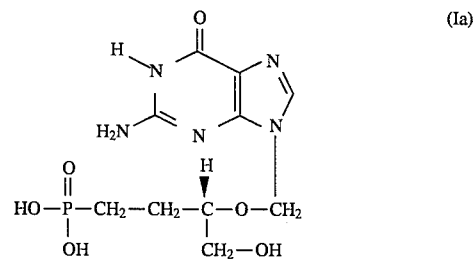

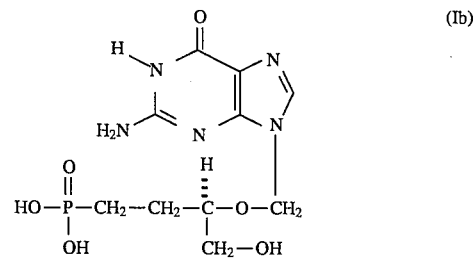

and may be in acid, salt or ester form. Such compounds may also be dehydrated to provide antiviral agents in cyclic form. Pharmaceutical compositions are provided containing the antiviral agents, as is a chiral synthesis which may be used to prepare the agents in enantiomerically pure form or as a racemic mixture.

3 Claims, No Drawings

ACYCLIC PURINE PHOSPHONATE NUCLEOTIDE ANALOGS AS ANTIVIRAL AGENTS, AND RELATED SYNTHETIC METHODS

ACKNOWLEDGEMENT OF GOVERNMENT SUPPORT

This invention was funded in part by the National Institute of Allergies and Infectious Diseases under contract number NO1-AI-72643. Accordingly, the United States government has certain rights in the invention.

TECHNICAL FIELD

This invention relates generally to the field of antiviral agents, and more particularly relates to enantiomerically pure acyclic purine phosphonate nucleotide analogs as antiviral agents. The invention additionally relates to pharmaceutical compositions containing the antiviral agents and to novel synthetic methods.

BACKGROUND

There are six known herpes-type viruses which affect human beings: herpes zoster (chicken pox), herpes simplex virus I & II (cold sores and genital herpes), cytomegalovirus (cytomegalic inclusion disease), Epstein-Barr virus (mononucleosis), and the recently isolated Herpes VI virus. The herpes viruses are medium-sized viruses containing double-stranded DNA, with a nucleocapsid about 100 nm in diameter surrounded by a lipid-containing envelope. The virion is 150–200 nm in diameter and permits latent infections which last for the life span of the host even when antibodies are present.

Purine-based analogs to treat herpes infections are known and have been described, for example, in U.S. Pat. No. 4,808,716 to Hol et al. and U.S. Pat. Nos. 4,755,516 and 4,897,479 to Tolman et al. The Hol et al. patent relates to 9-(phosphonylmethoxyalkyl)adenines and their use in treating herpes simplex virus, types I & II, while the Tolman et al. disclosures describe a family of 6-substituted purines which are stated to be useful against herpes viruses in general. U.S. Pat. No. 5,047,533 to Reist et al., of common assignment herewith, also describes purine analogs which have antiviral activity against the Herpes group of viruses. The present invention relates to and indeed derives from the work carried out in the aforementioned patent, and reference may be had thereto for information related to the present invention but not explicitly mentioned herein. Accordingly, the disclosure of U.S. Pat. No. 5,047,533 to Reist et al. is incorporated by reference in its entirety.

The antiviral agents of the present invention, like those of U.S. Pat. No. 5,047,533 to Reist et al., are acyclic purine phosphonate nucleotide analogs. In addition to the patents cited in the preceding paragraph, the following reference describes a large number of phosphonate analogs of nucleotides: R. Engle, *Chem. Reviews* 11(3):349–367 (1977). Phosphonate compounds which are direct cyclic nucleotide analogs are also disclosed in: U.S. Pat. No. 3,560,478 to Myers et al.; German Patent Application No. DE 3,045,375VA1, published Jul. 1, 1982; U.S. Pat. No. 3,446,793 to Jones et al.; British Patent Nos. 1,243,213 and 1,243,214; German Patent Application No. 2,009,834, published Sep. 17, 1970; A. Hampton et al., *Biochemistry* 12:1730–1736 (1973); G. H. Jones et al., *J. Am. Chem. Soc.* 90:5337–5338 (1968); and J. A. Montgomery et al., *J. Med. Chem.* 22:109–111 (1979).

Other references of interest include EPO Publication No. 173,624, published May 3, 1986, which discloses 9(3-phosphono-1-propoxymethyl)guanine as an anti-herpes agent, and A. E. Duke et al., *Antiviral Res.* 6:299–308 (1986) and E. J. Prisbe et al., *J. Med. Chem.* 29:671–675 (1986), which relate to 9(3-phosphono-1-hydroxymethyl-1-propoxymethyl) guanine.

The present invention in a first aspect relates to methods for making the acyclic purine phosphonate nucleotide analogs of the '533 patent in enantiomerically pure form. Prior to the development of the synthetic method described and claimed herein, neither isolation nor synthesis of the pure enantiomers was feasible. In another aspect, then, the invention encompasses enantiomerically pure acyclic purine phosphonate nucleotide analogs as novel compounds. Indeed, it has now been found that at least one of the isolated enantiomers—the "R" enantiomer—has significant activity against several herpes viruses. In still another aspect, the invention relates to the implementation of the aforementioned synthetic method—which may be used to make pure enantiomers, as noted above—to prepare the racemic mixture of acyclic purine phosphonate nucleotide analogs described in U.S. Pat. No. 5,047,533 to Reist et al., cited and incorporated by reference above.

SUMMARY OF THE INVENTION

It is accordingly a primary object of the invention to provide novel antiviral agents useful to treat herpes viral infections.

It is another object of the invention to provide such antiviral agents in the form of acyclic purine phosphonate nucleotide analogs.

It is still another object of the invention to provide such antiviral agents in enantiomerically pure form.

It is yet another object of the invention to provide methods for synthesizing the novel antiviral agents.

It is still another object of the invention to provide such synthetic methods which provide the novel antiviral agents as a racemic mixture of enantiomers.

It is yet another object of the invention to provide such synthetic methods which provide the novel antiviral agents in enantiomerically pure form.

It is a further object of the invention to provide pharmaceutical compositions for treating herpes viral infections.

It is still a further object of the invention to provide methods for treating herpes viral infections using the antiviral agents of the invention.

Additional objects, advantages and novel features of the invention will be set forth in part in the description which follows, and in part will become apparent to those skilled in the art upon examination of the following, or may be learned by practice of the invention.

In one aspect, then, the invention relates to antiviral agents having the structural formula (I)

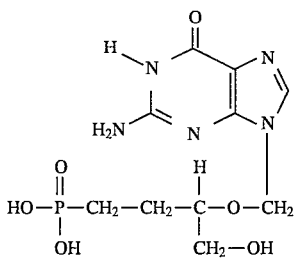
(I)

and to the corresponding (S) and (R) enantiomers (Ia) and (Ib):

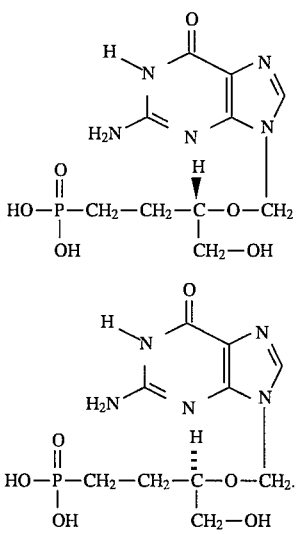
(Ia)

(Ib)

In another aspect, the invention relates to an antiviral agent having the structural formula (VIII)

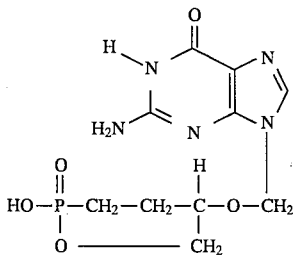
(VIII)

and to the corresponding (S) and (R) enantiomers (VIIIa) and (VIIIb):

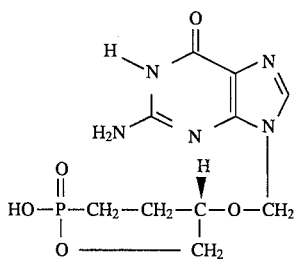
(VIIIa)

-continued

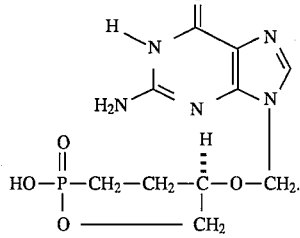
(VIIIb)

In other aspects, the invention relates to methods for synthesizing these compounds, preferably in enantiomerically pure form, or, alternatively, as a racemic mixture.

In still other aspects, the invention relates to pharmaceutical compositions containing the aforementioned compounds and to methods of using the compounds to treat herpes viral infections.

DETAILED DESCRIPTION OF THE INVENTION

Definitions and nomenclature:

Before the present compounds, compositions and methods are disclosed and described, it is to be understood that this invention is not limited to specific reagents or reaction conditions, specific pharmaceutical carriers, or to particular administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an antiviral agent" includes mixtures of antiviral agents, reference to "a pharmaceutical carrier" includes mixtures of two or more such carriers, and the like.

By the term "enantiomerically pure" as used herein is intended a composition containing at least about 90 wt. %, preferably at least 95 wt. %, most preferably at least 99 wt. %, of a single enantiomer.

By the term "alkyl" as used herein is meant a branched or unbranched saturated hydrocarbon chain of 1 to 20 carbon atoms. The term "lower alkyl" intends an alkyl group of 1 to 6 carbon atoms such as methyl, ethyl, n-propyl, isopropyl, t-butyl, and the like.

By the phrase "herpes viral infection" is meant infection with any one of the known herpes viruses, i.e., herpes simplex types I or II, cytomegalovirus, herpes zoster, Epstein-Barr virus, or herpes VI.

By the term "effective amount" of an antiviral agent is meant a nontoxic but sufficient amount of the agent to provide the desired treatment of viral infection. As will be pointed out below, the exact amount required will vary from subject to subject, depending on the species, age, and general condition of the subject, the severity of the infection, the particular antiviral agent and its mode of administration, and the like. Thus, it is not possible to specify an exact "effective amount." However, an appropriate effective amount may be determined by one of ordinary skill in the art using only routine experimentation.

By "pharmaceutically acceptable" is meant a material which is not biologically or otherwise undesirable, i.e., the material may be administered to an infected individual along with the selected antiviral agent without causing any undesirable biological effects or interacting in a deleterious manner with any of the other components of the pharmaceutical composition in which it is contained.

The purine moieties with which the present invention is concerned are purine moieties derived from either adenine or guanine, each of which has a nucleus of the formula

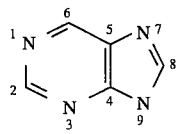

which has the numbering system shown. The numbering system will be retained herein as shown, regardless of substituents to the ring system. The bond at position 9 conjugates the acyclic or cyclic sugar derived moiety; further substitutions can be made at positions 2, 6 and 8.

For guanine, the substituent at position 6 is hydroxyl, and in adenine, $-NH_2$. Guanine has $-NH_2$ at position 2, while adenine is unsubstituted. Preferred compounds of the invention are guanine derivatives as shown in structural formula (I) and analogs containing modifications at positions 2, 6 or 8, i.e., analogs containing halo groups in place of the hydroxyl or amino at position 6, such as chloro or bromo in particular, are preferred. In general, suitable substituents at positions 2, 6 and 8 include hydroxyl, amino and halo wherein halo is defined as fluoro, chloro, bromo or iodo.

Synthetic method:

In one embodiment of the invention, a chiral synthesis is provided for preparing the antiviral agents of structural formulae Ia, Ib, VIIIa or VIIIb in enantiomerically pure form. As noted above, the synthesis may also be used to prepare the racemic mixture of compounds Ia and Ib, or of compounds VIIIa and VIIIb.

The synthesis involves providing as a starting material a hydroxy phosphonate compound having the structural formula

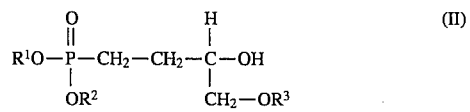

wherein $R^1$ and $R^2$ are independently selected from the group consisting of hydrogen and lower alkyl, and $R^3$ is lower alkyl or $-(CH_2)_n-C_6H_6)$ where n is an integer in the range of 0 to 6 inclusive. This starting material is then treated with gaseous HCl and paraformaldehyde under conditions effective to convert the 3-hydroxy group to a 3-chloromethyl ether substituents, conditions which typically involve reaction at temperatures below about 10° C., preferably temperatures approximatating 0° C. The 3-chloromethyl ether phosphonate (III) is thus provided:

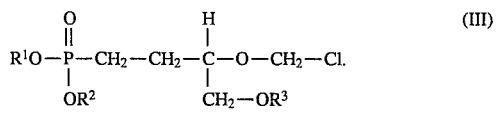

In the next step of the synthesis, compound (III) is admixed with 2-amino-6-chloropurine and a strong base, e.g., sodium hydride, in an organic solvent. Reaction is carried out at reflux for at least about 15 minutes, at which point the 9-substituted 2-amino-6-chloropurine (IV) may be isolated from the admixture:

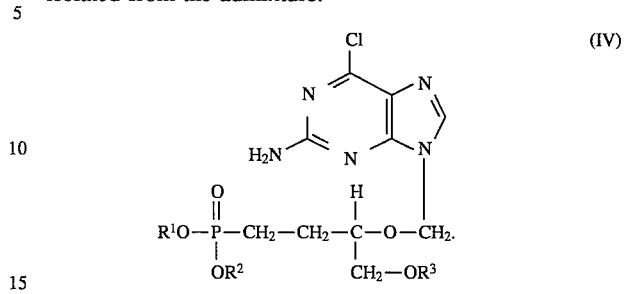

The 6-chloro functionality of compound (IV) is then converted to a 6-hydroxyethylthio moiety by treating compound (IV) with thioethanol, again in the presence of a strong base (e.g., sodium methoxide), at reflux. Reaction is allowed to proceed for at least about 30 minutes so as to provide the 2-amino-6-hydroxyethylthio derivative (V)

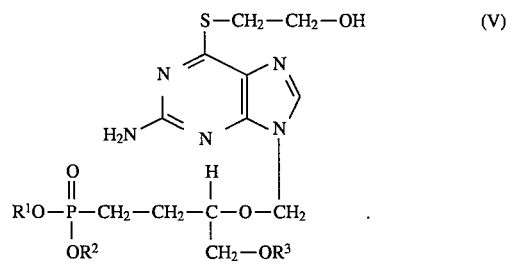

If $R^1$ and $R^2$ are other than hydrogen, i.e., if compound (V) is a phosphonic acid mono- or diester, it is converted to a phosphonate by treatment with a suitable reagent, e.g., bromotrimethylsilane. Such treatment provides the phosphonate (VI):

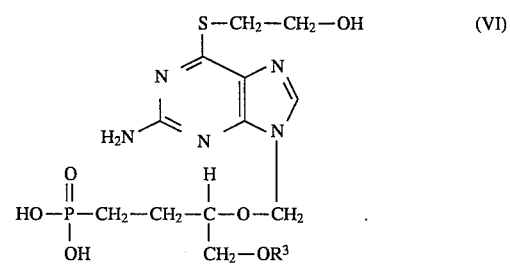

The 6-hydroxyethylthio moiety is then removed from compound (VI) by refluxing the compound with a strong base in the presence of water, for at least about ten hours. Compound (VII) results:

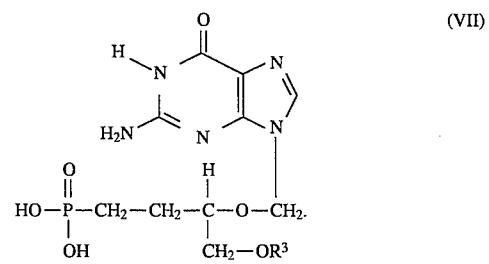

In the final step of the synthesis, compound (VII) is deprotected at $R^3$ to give rise to the desired compound (I)

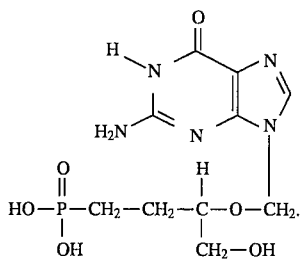

Deprotection may be effected using any suitable deprotecting reagent, i.e., a reagent which is effective to convert the $-OR^3$ moiety to an $-OH$ moiety but which will not adversely affect the remainder of the molecule. When $R^3$ is benzyl, an exemplary deprotecting reagent is $Pd(OH)_2$.

As the aforementioned procedure may be used in such a way that chirality of the starting material is maintained, the synthesis may be used to provide compound (Ia) in enantiomerically pure form using (IIa) as the starting material

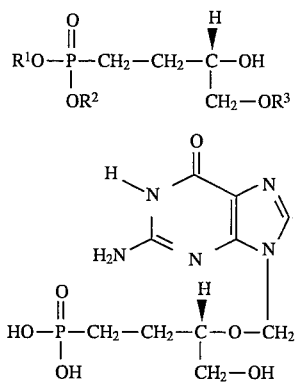

or to provide compound (Ib) in enantiomerically pure form using (IIb) as the starting material.

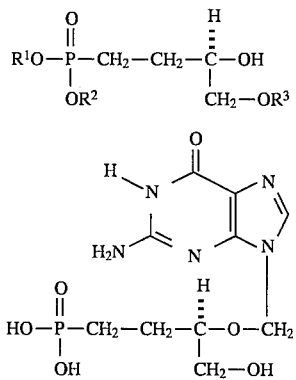

Cyclic compounds (VIIIa) and (VIIIb) may then be synthesized directly from compounds (Ia) and (Ib), respectively, via a formal dehydration reaction in the presence of a dehydrating agent such as N',N'-dicyclohexyl-4-morpholine carboxamidine.

Enantiomerically pure compounds Ia, Ib, VIIIa and VIIIb, as well as the synthetic intermediates represented by structural formulae IVa, IVb, Va, Vb, VIa, VIb, VIIa and VIIb are novel compounds and, as noted above, may be substituted at the 2, 6 and/or 8 positions with hydroxyl, amino or halo substituents. Modification at the 2-position may be effected at any point during the above-described synthesis, using conventional techniques as will be appreciated by those skilled in the art of synthetic organic chemistry. Typically, the amino group initially present at the 2-position is activated with a suitable activating agent and replaced, for example, with a halogen or hydroxyl substituent. Modification at the 6-position is carried out prior to synthesis of the 6-hydroxyethylthio derivative (V). Such modification will generally involve removal and replacement of the 6-chloro functionality in compounds I, II or IV using standard chemistry. Modification at the 8-position may be carried out at any time during the synthesis, and, again, may be done using standard chemical techniques. Typically, modification at the 8-position will involve bromination followed by displacement of the 8-bromo functionality with an azide, thiol, or the like.

The compounds may also be converted to salt and/or ester derivatives, as follows, and such compounds are also within the scope of the present invention.

Phosphonic Acid Salts: If desired, the free phosphonic acid of compounds Ia or IIa may be converted to the mono- or dibasic salt form by treatment with an appropriate base. These salts are prepared by treating the corresponding free acids with at least one or at least two molar equivalents of a pharmaceutically acceptable base as set forth above. The reaction is conducted in water, alone or in combination with an inert, water-miscible organic solvent at a temperature of from 0° C. to about 100° C., preferably at about room temperature. Typical inert, water-miscible organic solvents include methanol, ethanol and dioxane. The stoichiometry of the resulting salt is dependent on the stoichiometry of the reaction components.

The salts can be reconverted to the phosphonic acid by standard procedures, e.g., by neutralizing with an acid resin or, less preferably, with an organic acid.

Acid Addition Salts: Alternatively, acid addition salts of the purine moiety may be prepared by reacting a compound of the invention with an acid such as the organic or inorganic acids exemplified above. The free base is dissolved in a polar organic solvent such as methanol or ethanol and the acid is added at a temperature of about 0° C. to about 100° C., preferably at about room temperature. The resulting salt either precipitates or may be brought out of solution by addition of a less polar solvent.

Conversely, the acid addition salt is reconverted to the free base by treating with suitable base.

Phosphonic Acid Esters: Desired esters of the phosphonic acid moiety may be prepared by transesterification of the phenyl esters using methods illustrated by Jones and Moffatt, *J. Am. Chem. Soc.* 90:5337 (1968). The esters can be reconverted to the free acids by hydrogenolysis or hydrolysis. These esters may be prepared by transesterification as above described.

Utility and Administration:

The compounds of the invention defined by structural formulae Ia, Ib, VIIIa and VIIIb, including the physiologically acceptable salts and esters thereof, have antiviral activity against one or more herpes viral infections. In addition, the novel synthetic intermediates represented by structural formulae IVa, IVb, Va, Vb, VIa, VIb, VIIa and VIIb are also believed to be useful as antiviral prodrugs, and may accordingly be administered to treat herpes viral infections as well. The compounds may be conveniently formulated into pharmaceutical preparations composed of one or more of the compounds in association with a pharmaceutically acceptable carrier. *Remington's Pharmaceutical Sciences*, latest edition, by E. W. Martin (Mack Publ. Co., Easton, Pa.) discloses typical carriers and methods of preparation known in the art.

The compounds may be administered topically, orally, parenterally (e.g., intravenously), by intramuscular injection, or by intraperitoneal injection, or the like, depending on the nature of the herpes viral infection being treated. For internal infections the compositions are administered orally or parenterally at dose levels of about 0.1 to 300 mg/kg, preferably 1.0 to 30 mg/kg of mammal body weight and can be used in humans in a unit dosage form administered one to four times daily in the amount of 1 to 250 mg per unit dose.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Alternatively, for topical infections, e.g., mouth and skin, the compositions are preferably applied to the infected part of the body of the patient topically as an ointment, cream, aerosol or powder, preferably as an ointment or cream. The compounds may be presented in an ointment, for instance with a water-soluble ointment base, or in a cream, for instance with an oil in water cream base in a concentration of from about 0.01 to 10%, preferably 0.1 to 7%, most preferably about 0.5% w/w. Additionally, viral infections of the eye, such as Herpetic keratitis, may be treated by use of a sustained release drug delivery system as is know in the art.

The exact regimen for administration of the compounds and compositions disclosed herein will necessarily be dependent upon the needs of the individual subject being treated, the type of treatment and the judgment of the attending practitioner.

EXPERIMENTAL

The following examples are put forth so as to provide those of ordinary skill in the art with a complete disclosure and description of how to carry out the synthetic methods of the invention and make the enantiomerically pure antiviral agents claimed herein, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

Example 1 describes preparation of the compound having the structural formula 1-9 as shown in Scheme 1. Briefly, the synthesis set forth in Scheme 1 involves, initially, transformation of the (R) glycidyl tosylate 1-1 to the (S) glycidyl benzylether 1-3 using the procedure described by H.-S. Byun et al., *Tetrahedron Lett.* 30:2751 (1989) (Example 1, sections (a.) and (b.)). The epoxide was then opened regiospecifically with lithiated diethyl methylphosphonate in the presence of boron trifluoride etherate to afford 1-4 in 68% yield (Example 1, section (c.)). Based on the measurement of the optical rotation, no racemization was observed in this step. Compound 1-4 was then transformed to the corresponding chloromethyl ether and condensed with 2-amino-6-chloropurine in the presence of sodium hydride to give the nucleoside phosphonate 1-5 in 45% yield (Example 1, section (d.)). Treatment of 1-5 with thioethanol in the presence of sodium methoxide gave a 2:1 mixture of the thioethanol derivative 1-6 and of the corresponding guanine. By working in anhydrous conditions the thioethanol derivative 1-6 was obtained in 90% yield (Example 1, section (e.)). Treatment of 1-6 with an excess of bromotrimethylsilane in hexamethyldisilazane gave the phosphonic acid 1-7 which without further purification was treated with sodium methoxide to give the guanine derivative 1-8 in 82% yield over the two last steps (Example 1, sections (f.) and (g.)). Finally, the benzyl ether was removed by transfer hydrogenation using palladium hydroxide in the presence of cyclohexene to give the desired nucleoside phosphonate 1-9 in 90% yield (Example 1, section (h.)). Optical purity of all compounds may be determined by HPLC using a chiral column.

Example 2 describes preparation of the corresponding (R) isomer, using the route shown in Scheme 2, while Examples 3 and 4 describe how the synthesis may be used to prepare either the racemic mixture or analogs of the antiviral agents prepared in Examples 1 and 2. Example 5 describes preparation of a cyclic analog. Antiviral activity is evaluated in Example 6.

Scheme 1

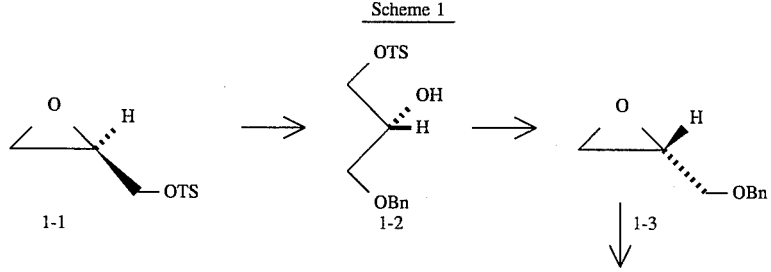

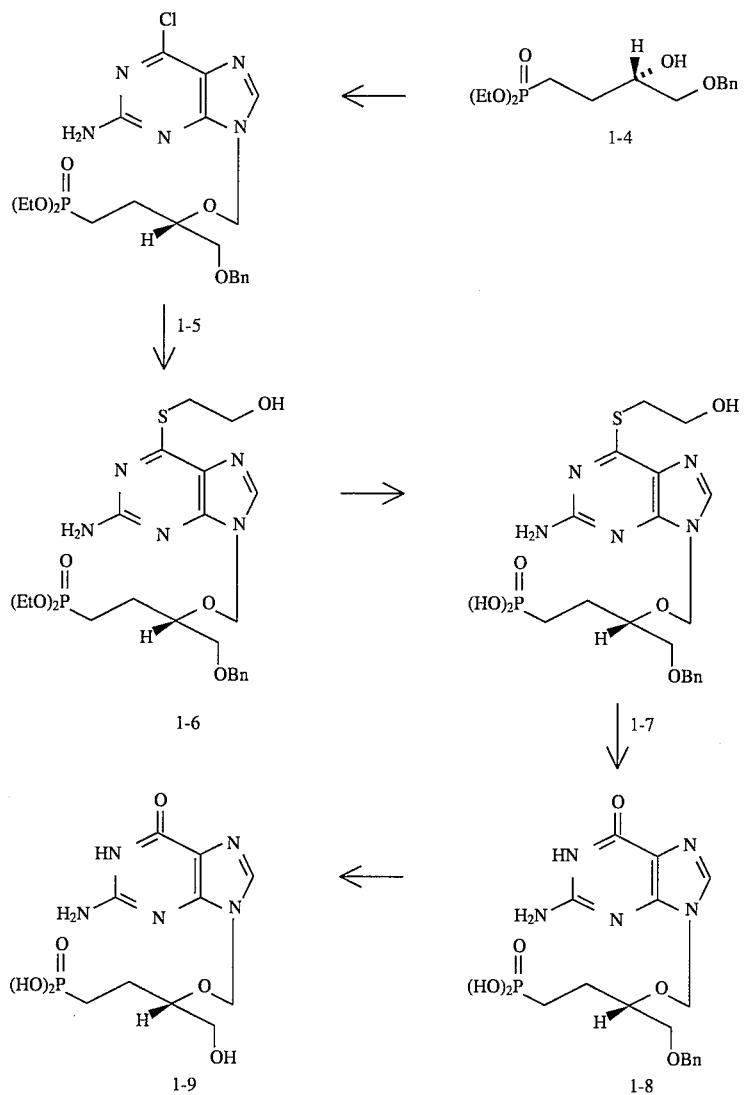
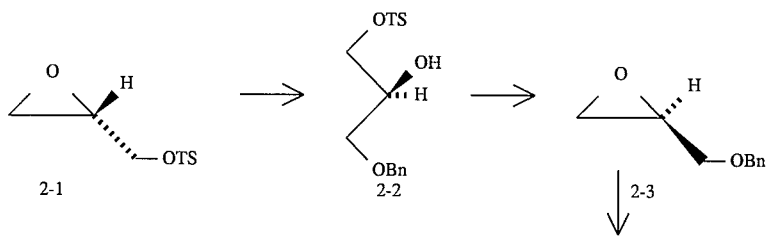

-continued
Scheme 2

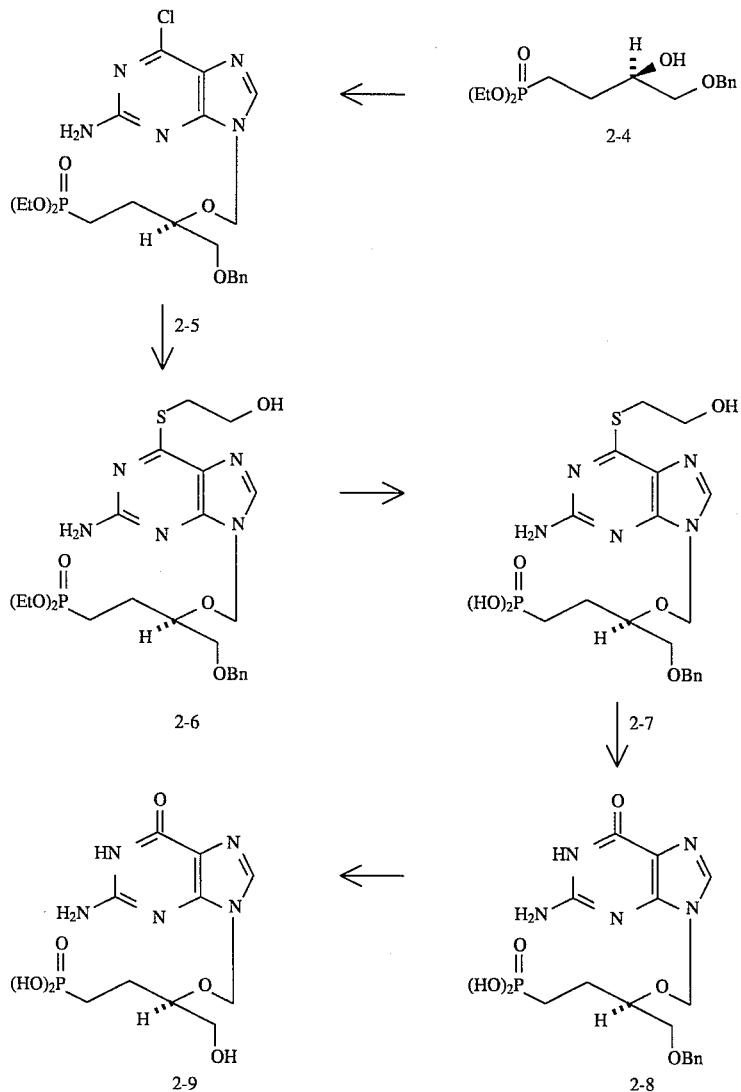

EXAMPLE 1

(a.) Preparation of R(−)-1-O-benzyl-3-O-p-tolylsulfonyl-(sn)-glycerol (1-2)

To a solution of 10.6 g (46 mmoles) of 2R(−)-glycidyl tosylate 1-1 containing 5 g of 3 Å molecule sieves and 9.43 mL (92 mmoles) of benzyl alcohol in 100 mL of dichloromethane at 0° C. was added 560 μL (4.4 mmoles) of boron trifluoride etherate. The mixture was stirred overnight at 0° C., warmed to room temperature and filtered through a celite pad. The filtrate was washed with 10% aqueous NaHCO$_3$, brine, dried over Na$_2$SO$_4$, and concentrated to give a colorless oil which precipitated from hexane-ether. The precipitate was filtered and recrystallized once from ether-petroleum ether, giving 14 g (91%) as a white solid [α]$_D^{25}$= −7.07 (C=10, C$_6$H$_6$); lit [α]$_D^{25}$=−6.70 (C=10, C$_6$H$_6$).

$^1$H NMR (300 MHz, CDCl$_3$) d=7.79 (d, J=8.4 Hz, 2H), 7.26–7.35 (m, 5H), 4.50 (s, 2H), 3.97–4.13 (m, 3H), 3.51–3.53 (m, 2H), 2.45 s, 3H), 2.30 (bs, 1H).

(b.) Preparation of 2S-(+) -Benzylglycidyl ether (1-3)

To a solution of 13.4 g (39.8 mmoles) of 1-2 in 160 mL of methanol at −10° C. was added 6.6 g (47.8 mmoles) of powdered K$_2$CO$_3$. The mixture was stirred for 2 h at −10° C., then for 2 h at room temperature. Ether (200 mL) was added and the mixture was filtered through a pad of silica gel. The solvents were removed and the residue was dissolved in dichloromethane (100 mL), washed with brine and dried over Na$_2$SO$_4$. Removal of the solvents gave a yellow liquid which was purified by flash chromatography (silica, 5% ethylacetate in hexane) to give 5.9 g (90%) of a colorless liquid [α]$_D$=+6.4 (C=4.9, C$_6$H$_6$); lit [α]$_D$=+5.4 (C=5, C$_6$H$_6$); $^1$H NMR (300 MHz, CDCl$_3$) S=7.26–7.37 (m, 5H), 4.59 (dd, J=20, 12 Hz, 2H) 3.77 (dd, J=11.26, 3.02 Hz, 1H), 3.45 (dd, J=11.4, 5.9 1H), 3.18–3.22 (m, 1H), 2.88 (t, J=4.62 Hz, 1H), 2.63 (dd, J=4.97, 2.71 Hz, 1H). Alternatively, compound 1-3 may be obtained commercially, e.g., from the Aldrich Chemical Company, Milwaukee, Wis.

(c.) Preparation of Diethyl 2S(−)-4-O-benzyl-3,4-dihydroxybutylphosphonate (1-4)

To a solution of diethyl methylphosphonate (373 μL, 2.2 mmoles) in THF (10 mL) was slowly added a solution of n-butyllithium (1.69 mL, 2.7 mmoles, 1.6M in hexane) at −78° C. After 10 minutes, $BF_3OEt_2$ (300 μL, 2.43 mmoles) was added. To the resulting solution was slowly added (over 15 minutes) a solution of the epoxide 1-3 (300 mg, 1.83 mmoles in THF (3 mL). The mixture was stirred for 15 minutes at −78° C. and kept overnight at −15° C. Then it was diluted with dichloromethane (20 mL) washed with aqueous $NaHCO_3$, brine, and dried ($MgSO_4$). The solvents were removed under vacuum and the residue was purified by flash chromatography (silica, 3% of isopropanol in ethylacetate) to give a pale yellow oil (467 mg, 68%). $[\alpha]_D=-10.2$ (C=2.85, $C_6H_6$); $^1H$ NMR (300 MHz, $CDCl_3$) δ=7.29–7.33 (m, 5H), 4.55 (s, 2H), 4.03–4.15 (m, 2H), 3.8–3.9 (m, 1H), 3.48 (dd, J=7.5, 3.85 Hz, 1H), 3.34–3.40 (dd, J=9.41, 6.97 Hz, 1H), 2.61 (s, 1H), 1.65–2.05 (m, 4H), 1.31 (t, J=7 Hz, 6H). $^{13}C$ (75 MHz, $CDCl_3$) 16.44, 16.52, 20.95, 22.83, 26.32, 26.39, 61.63, 61.71, 70.08, 70.27, 73.44, 73.98, 76.65, 77.07, 77.50, 127.78, 127.85, 128.50, 138.00.

(d.) Preparation of 2-Amino-6-chloro-9-[(S(+)-1-benzyloxymethyl-3-diethylphosphono)-3-propyloxymethyl]-9H-Purine (1-5)

A suspension of alcohol 1-4 (200 mg, 632 mmole) in dry 1,2-dichloroethane (20 mL) and paraformaldehyde (60 mg) was treated for 2 hr at −10° C. with gaseous HCl. Argon was then bubbled through the resulting solution for 10 min at room temperature. The solution was dried over $CaCl_2$, filtered evaporated to dryness and resolubilized in dimethylformamide (2 mL) for addition to the solution of the purine sodium salt as follows:

2-Amino-6-chloropurine (120 mg, 695 mmole; obtained from Aldrich) was suspended in dimethylformamide (1.5 mL) and treated with NaH (31 mg, 60% in oil, 764 mmole) for 1 hr at room temperature. To the resulting solution was added the solution of chloromethyl ether at −20° C. After 1 hr of stirring at −20° C., the reaction mixture was partitioned between 10 mL each of saturated aqueous sodium bicarbonate and dichloromethane. The dichloromethane solution was washed with 10 mL water, dried over $MgSO_4$ and evaporated to dryness in vacuo. The crude product was purified by chromatography on silica gel using dichloromethane/methanol (39:1) to give 140 mg (45%) of product with $[\alpha]_D^{22}=+9.9$ (C=1, $C_6H_6$) $^1H$ NMR (300 MHz, $CDCl_3$): 7.86 (s, 1H); 7.25–7.34 (m, 5H); 5.59 (s, 2H); 5.3–5.5 (bs, 2H); 4.48 (s, 2H); 3.98–4.09 (m, 4H); 3.78–3.88 (m, 1H); 3.44 (dd, J=4.6, 2.8 Hz, 2H); 1.55–2.05 (m, 4H); 1.27 (td, J=7, 1.7 Hz, 6H).

(e.) Preparation of 2-Amino-6-hydroxyethylthio-9-[(S(+)-1-benzyloxymethyl-3-diethylphosphono)propyloxymethyl)] 9H-purine (1-6)

A solution of 1-5 (150 mg, 0.3 mmole) in dry methanol (20 mL) was treated with thioethanol (64 μL, 0.9 mmole) in the presence of NaOMe (49 mg, 0.9 mmole) at reflux for 45 minutes. The reaction mixture was cooled to room temperature and the solvents were evaporated to dryness. The residue was dissolved in chloroform and washed with brine after adjusting the pH to 7. The organic layer was dried over $Na_2SO_4$ and the solvents were removed. The residue was purified by preparative thin layer chromatography (5% methanol in dichloromethane) to give 147 mg (90%) of 1-6. $[\alpha]_D=+6.6$ (C=4.87, $C_6H_6$). $^1N$ NMR (300 MHz, $CDCl_3$) 7.77 (s, 1H), 7.24–7.38 (m, 5H), 5.56 (s, 2H), 5.25 (bs, 2H), 4.49 (s, 2H), 3.93–3.98 (m, 4H), 3.96 (t, J=5.6 Hz, 2H), 3.39–3.51 (m, 4H), 1.5–1.88 (m, 4H), 1.27 (t, J=6.6 Hz).

$^{13}C$ (75 MHz, $CDCl_3$) δ=16.43, 16.51, 20.27, 22.16, 24.32, 24.37, 32.20, 61.63, 61.71, 63.03, 71.98, 72.73, 73.49, 76.67, 77.09, 77.22, 77.43, 77.51, 125.8, 127.67, 127.86, 128.51, 136.8, 140.61, 151.5, 159.2, 161.7.

(f.) Preparation of 2-Amino-6-hydroxyethylthio-9-[(S)-1-benzyloxymethyl-3-phosphono)propyloxymethyl) 9H-purine (1-7)

A solution of 1-6 (146 mg, 0.27 mmole) in a 1:1 mixture of dichloromethane (6 mL) and hexamethyldisilazane (6 mL) was treated with bromotrimethyl silane (360 μL, 2.7 mmoles) for 3 hr at room temperature. Then the solvents were removed and the residue was redissolved in a 1:1 mixture of ethanol and water. The solvents were removed to dryness to give 130 mg of a white powder. $^1H$ NMR (300 MHz, MeOD) δ=8.01 (s, 1H), 7.23–7.32 (m, 5H), 5.61 (s, 2H), 4.41 (s, 2H), 3.93 (bs, 1H), 3.80 (t, J=6.5 Hz, 2H), 3.38–3.48 (m, 4H), 1.4–1.95 (m, 4H).

(g.) Preparation of 9-[(S(+)-Benzyloxymethyl-3-phosphono)propyloxymethyl]-guanine (1-8)

A solution of the purine 1-7 (130 mg, 0.27 mmole) in methanol (12 mL) was treated at reflux with NaOMe (146 mg, 2.7 mmoles) in the presence of water (8 μL, 0.405 mmole) for 18 hr. The reaction mixture was cooled to room temperature and the solvents were evaporated to give a white solid which was purified on a reverse phase column ($C_{18}$ silica, water/methanol) to give 87 mg (76% over the two last steps) of a white solid. $[\alpha]_D=+39.8$ (C=0.77, $H_2O$). $^1H$ NMR (400 MHz, $D_2O$) 7.80 (s, 1H), 7.24–7.26 (m, 3H), 7.02–7.04 (m, 2H), 5.49 (d, J=11.6 Hz, 1H), 5.37 (d, J=11.6 Hz, 1H), 4.27 (dd, J=16, 11.85 Hz, 2H), 3.75–3.82 (m, 1H), 3.2 (dd, J=11.4, 2.5 Hz, 1H), 3.35 (dd, J=11.3, 7.24 Hz, 1H), 1.65–1.8 (m, 2H), 1.4–1.6 (m, 2H); $^{13}C$ (75 MHz, $D_2O$) δ=22.7, 25.40, 25.44, 71.53, 72.33, 72.77, 78.78, 79.01, 116.2, 127.74, 128.06, 128.49, 137.6, 139.87, 151.8, 153.9, 158.5.

The R-isomer had $[\alpha]_D$ −46° (C=0.77, $H_2O$).

(h.) 9-[(S(+)-1-Hydroxymethyl-3-phosphono)propyl-oxymethyl] guanine (1-9)

The benzylether 1-8 (80 mg, 0.19 mmole) in 21 mL of a 1:1:1 mixture of freshly distilled cyclohexene, ethanol and water was treated at reflux with $Pd(OH)_2$ (110 mg, 50% wet) for 24 hr. The suspension was cooled to room temperature, filtered through a celite pad which was washed several times with hot water. The filtrate was evaporated to dryness and the residue was triturated with methanol, filtered to give 55 mg (90%) of a white solid. $[\alpha]_D=+3$ (C=0.68, $H_2O$). $^1H$ NMR (400 MHz, $D_2O$) δ=7.9 (bs, 1H), 5.52 (dd, J=15, 11.35 Hz, 2H), 3.62–3.69 (m, 1H), 3.6 (dd, J=12.3, 3.3 Hz, 1H), 1.5–1.7 (m, 2H) 1.2–1.5 (m, 2H); $^{13}C$ NMR (75 MHz, $D_2O$) δ=24.09, 25.43, 25.95, 64.07, 64.1, 66.02, 73.16, 117.38, 141.31, 155.26, 160.16, 183.07.

EXAMPLE 2

The procedure of Example 1 was repeated so as to carry out the synthesis illustrated in Scheme 2, to prepare the corresponding (R) isomer, compound 2-9.

(a.) The procedure of Example 1, part (a.), was repeated using 2S(+)-glycidyl tosylate 2-1. The enantiomer S(+) 2-2 was prepared in 85% yield. $[\alpha]_D^{25}$=+5.45 (C=10, $C_6H_6$; lit $[\alpha]D$=+6.79 (C=10, $C_6H_6$).

(b.) The procedure of Example 1, part (b.), was followed to prepare enantiomer 2-3 from 2-2 in 92% yield. $[\alpha]_D^{25}$= –6.39 (C=5.1, $C_6H_6$); lit $[\alpha]_D$=–5.35 (C=5, $C_6H_6$).

(c.) Preparation of Diethyl-2R(+)-4-O-benzyl-3,4-dihydroxybutylphosphonate (2-4)

n-Butyllithium (1.6M in hexane, 33.75 mL, 54 mmol) was added dropwise to a solution of diethylmethylphosphonate (7.9 mL, 54 mmol) in dry THF (60 mL) at –78° C. After 30 min of stirring at –78° C., the resulting white suspension was added dropwise through a canular to a stirred solution of $BF_3OEt_2$ (6.64 mL, 54 mmol) in THF (120 mL) at –78° C. After 10 min neat 2R(–)benzylglycidylether as synthesized in the preceding section (compound 2-3; 3 g, 18 mmol) was added quickly to this suspension. After 30 min of stirring at –78° C., the reaction was quenched by addition of saturated $NaHCO_3$ (30 mL) and allowed to warm to room temperature. The reaction mixture was poured into ether (300 mL) and washed with saturated $NaHCO_3$. The aqueous layer was extracted three times with ether (150 mL), concentrated and extracted with $CH_2Cl_2$ (150 mL). The combined organic layers were washed with saturated NaCl and dried over $MgSO_4$. The solvents were removed and the residue was pumped at 80° C. under 1 mm Hg to remove the excess of diethylmethyl phosphonate. The crude product (90% pure) was purified by flash chromatography (silica: EtOAc/Isopropanol: 97.5/2.5) to afford pure 2-4 (5.4 g, 95%) as a faint yellow liquid; $R_f$=0.43 ($CH_2Cl_2$/MeOH: 95/5); $[\alpha]_D^{22}$=+9.1 (c=3.3, benzene); EI-mass spectrum m/z 317 ($M+H^+$), 195, 121, 91; FABHRMS Calcd for $C_{15}H_{26}PO_5$ 317.1518 ($M+H^+$), found 317.1508; $^1$H NMR (300 MHz, $CDCl_3$) d=7.29–7.33 (m, 5H), 4.55 (s, 2H), 4.03–4.15 (m, 2H), 3.80–3.90 (m, 1H), 3.49 (dd, J=7.5, 3.85 (Hz, 1H), 3.38 (dd, J=9.4, 6.9 Hz, 1H), 2.61 (s, 1H), 1.65–2.05 (m, 4H), 1.31 (d, J=7 Hz, 6H); $^{13}$C (75 MHz, $CDCl_3$) d=138.00, 128.50, 127.85, 127.78, 77.50, 77.07, 76.65, 73.98, 73.44, 70.27, 70.08, 61.71, 61.63, 26.39, 26.32, 22,83, 20.95, 16.52, 16.44.

(d.) Preparation of 2-Amino-6-chloro-9-[(R(–)-1-benzyl-oxymethyl-3-diethylphosphono)-3-propyloxymethyl]-9H-purine (2-5)

A suspension of alcohol 2-4 (6 g, 18.9 mmol) in dry DCE (110 mL) and paraformaldehyde (1.5 g) was treated for 2 hrs at –10° C. with gaseous HCl. Then argon was bubbled through the resulting solution for 10 min at room temperature. The solution was dried over $CaCl_2$, filtered, evaporated to dryness and resolubilized in DMF (30 mL) for addition to the solution of purine sodium salt prepared as follows: 2-amino-6-chloropurine (3.83 g, 22.6 mmol) was suspended in DMF (40 mL) and treated with NaH (0.95 g, 60% in oil, 23.7 mmol) for 1 hr at room temperature. The solution of chloromethylether was added to the resulting solution at –78° C. After 1 hr of stirring at –20° C., the reaction mixture was poured in $CH_2Cl_2$ (150 mL), washed with saturated $NaHCO_3$. The aqueous layer was extracted three times with $CH_2Cl_2$ (100 mL), dried over $Na_2SO_4$ and evaporated. The crude product was purified by column chromatography (silica; $CH_2Cl_2$/MeOH: 97.5/2.5) to give pure R(–) 2-5 (4.7 g, 50%) as a colorless thick oil; $R_f$=0.35 ($CH_2CL_2$/MeOH: 95/5); $[\alpha]_D^{23}$=–6.8, c=1.03, benzene; EI-mass spectrum, m/z 497 ($M^+$), 329; FABHRMS calcd for $C_{21}H_{30}ClN_5O_5P$ 498.1673, ($M+H^+$), found 498.1663; $^1$H NMR (300 MHz, $CDCl_3$) d=7.82 (s, 1H), 7.15–7.35 (m, 5H), 5.80–6.05 (broad s, 2H), 5.52 (2H, s), 4.06 (s, 2H), 3.90–4.05 (m, 4H), 3.73–3.82 (m, 1H), 3.38 (d, J=4.9 Hz, 2H), 1.50–1.80 (m, 4H), 1.15–1.28 (t, J=7 Hz, 6H); $^{13}$C NMR (75 MHz, $CDCl_3$) d=159.80, 153.80, 151.50, 142.32, 136.80, 128.45, 127.83, 127.61, 125.05, 77.59. 77.40, 73.42, 72.42, 72.75, 72.32, 61.68, 61.60, 24.40, 22.08, 20.19, 16.47, 16.40.

(e.) 2-Amino-6-hydroxyethylthio-9-[(R(–)-1-benzyl-oxymethyl-3-diethylphophono)propyloxymethyl]-9H-purine (2-6)

A solution of R(–) 2-5 (4 g, 8 mmol) in dry methanol (90 mL) was treated with thioethanol (1.7 mL, 24 mmol) in the presence of NaOMe (1.3 g, 24 mmol) at reflux for 2 hrs. The reaction mixture was cooled to room temperature and the solvents were evaporated to dryness. The residue was dissolved in water and the pH was adjusted to approximately 7. The aqueous layer was extracted three times with chloroform (150 mL) and the combined organic layers were washed with brine and dried over $Na_2SO_4$. The solvents were removed and the residue was purified by flash chromatography (silica: $CH_2Cl_2$/MeOH; 97.5/2.5) to give pure 2-6 (3.9 g, 90%) as a colorless oil; $R_f$=0.21 ($CH_2Cl_2$/MeOH: 95/5); $[\alpha]_D^{22}$=–8.4, c=3.45, benzene); $^1$H NMR (300 MHz, $CDCl_3$) d=7.75 (s, 1H), 7.24–7.42 (m, 5H), 5.54 (s, 1H), 5.40 (broad s, 2H), 4.47 (s, 2H), 3.98–4.10 (m, 4H), 3.82 (t, J=5.6 Hz, 2H), 3.76–3.86 (m, 1H), 3.42–3.52 (m, 4H), 1.50–1.88 (m, 4H), 1.27 (t, J=6.6 Hz, 6H); $^{13}$C NMR (75 MHz, $CDCl_3$ d=161.70, 159.20, 151.50, 140.59, 136.80, 128.50, 127.85, 127.66, 125.8, 77.51, 77.22, 73.47, 72.70, 71.98, 62.84, 61.74, 61.65, 32.07, 24.37, 24.31, 22.11, 20.22, 16.49, 16.42.

(f.) 2-Amino-6-hydroxyethylthio-9-[(R(–)-1-benzyl-oxymethyl-3-phosphono)propyloxymethyl]-9H-purine (2-7)

A solution of 2-6 (3.75 g, 6.9 mmol) in a 1:1 mixture of $CH_2Cl_2$ (50 mL) and hexamethyldisilazane (50 mL) was treated with bromotrimethylsilane (9.1 mL, 69 mmol) for 6 hrs at room temperature. The solvents were removed and the residue was dissolved in a 1:1 mixture of ethanol-water (100 mL). The solvents were evaporated to dryness to give crude 2-7 as a white powder that was used without purification for the preparation of 2-8; $^1$H NMR (300 MHz, $CD_3OD$) d=8.01 (s, 1H), 7.23–7.32 (m, 5H), 5.62 (s, 2H), 4.41 (s, 2H), 3.90–3.98 (m, 1H), 3.82 (t, J=6.7 Hz, 2H), 3.38–3.54 (m, 4H), 1.40–1.90 (m, 4H).

(g.) 9-[(R(–)-Benzyloxymethyl-3-phosphono)propyl-oxymethyl]guanine (2-8)

A solution of the purine 2-7 (theo. 6.9 mmol) in methanol (300 mL) was treated at reflux with NaOMe (3.72 g, 69 mmol) in the presence of water (200 μL, 10 mmol) for 16 hrs. The reaction mixture was cooled to room temperature and the solvents were evaporated to give a white solid which was purified by reverse phase column ($C_{18}$ silica, $H_2O$) to give pure 2-8 (2.8 g, 91% over the two last steps); Rf=0.33 (CH$_3$CN/NH$_4$Cl: 7/3); [α]$_D^{22}$=–46, c=0.8 in H$_2$O; EI-mass spectrum m/z 639 (MTMS$_3^+$), 417; FABHRMS Calcd for C$_{17}$H$_{22}$NaN$_5$O$_6$P 446.1205 (M+H$^+$), found 446.1183; $^1$H NMR (400 MHz, CD$_3$OD) d=7.79 (s, 1H), 7.10–7.32 (m, 5H), 5.54 (s, 2H), 4.40 (s, 2H), 3.84–3.91 (m, 1H), 3.48 (dd, J=10, 3.2 Hz, 1H), 3.41 (dd, J=10.6, 7.14, 1H), 1.76–1.88 (m, 2H), 1.35–1.59 (m, 2H); $^{13}$C (100 MHz, CD$_3$OD) d=161.52, 156.95, 153.25, 139.64, 139.54, 129.27, 128.68, 128.52, 117.62, 80.33, 80.17, 74.21, 73.08, 27.79, 27.76. 27.16, 25.86.

(h.) 9-[(R(–)-1-Hydroxymethyl-3-phosphono)-propyl-oxymethyl]guanine (2-9)

The benzyl ether 2-8 (2.6 g, 5.3 mmol) in a mixture of cyclohexene (80 mL), ethanol (150 mL) and H$_2$O (80 mL) was treated at reflux with Pd (OH)$_2$ (1.2 g, 50% wet) for 15 hrs. The hot solution was filtered two times and the solvents were evaporated to dryness to give pure 2-9 (1.6 g, 87%); Rf=0.22 (CH$_3$CN/NH$_4$Cl: 7/3); [α]$_D^{22}$=–2, c=0.85 in H$_2$O; UV max(H$_2$O) at pH 1, 256 nm (e 12708), 275 sh (8692); at pH 7, 252 nm (13445), 271 sh (9366); at pH 11, 259 sh (11312); EI-mass spectrum, m/z 621 (MTMS$_4^+$), 399, 369, 147; FABHRMS calcd for C$_{10}$H$_{16}$NaN$_5$O$_6$P 356.0736 (M+H$^+$), found 356.0758; $^1$H NMR (400 MHz, D$_2$O) d=7.80 (s, 1H), 5.55 j (d, J=12.02 Hz, 1H), 5.51 (d, J=11.35 Hz, 1H), 3.64–3.71 (m, 1H), 3.61 (dd, J=12.25, 3.46 Hz, 1H), 3.47 (dd, J=12.27, 6.05 Hz, 1H), 1.52–1.68 (m, 2H), 1.22–1.51 (m, 2H); $^{13}$C (100 MHz, D$_2$O) d=176.80, 160.12, 155.72,. 153.03, 141.25, 116.94, 81.65, 81.48, 73.70, 64.45, 26.36, 26.32, 25.72, 24.38.

(h.) The procedure of Example 1, part (h.), was repeated to prepare enantiomer 2-9 from compound 2-8. This R(–) enantiomer had [α]$_D$=–3.45° (C, 0.75, H$_2$O).

EXAMPLE 3

The procedure of the foregoing examples may be used to make the racemic mixture of compounds 1-9 and 2-9, using a a racemic mixture of glycidyl tosylate enantiomers 1-1 and 2-1 in part (a.) of the synthesis.

EXAMPLE 4

The procedure of the foregoing examples may be used to make acyclic purine phosphonate nucleotide analogs identical to compounds 1-9 and 2-9, but containing modifications as shown in structural formula (I), and using appropriately substituted reactants.

EXAMPLE 5

Preparation of 9-(R-3'-Phosphono-1'-hydroxymethyl-1'-propyloxymethyl) guanine, cyclic ester (3)

The sodium salt of 9-[(R(–)-1-hydroxymethyl-3-phosphono)-propyl-oxymethyl]guanine (2-9) (300 mg, 0.84 mmol) was suspended in pyridine and treated with N,N'-dicyclohexyl morpholine carboxamidinium salt (250 mg, 0.884 mmol). The suspension was heated to reflux, a hot solution of 382 mg (1.85 mmole) of DDC in pyridine (60 ml) was added. The reaction was heated at reflux overnight and then evaporated to dryness in vacuo. The residue was triturated with water and filtered. The filter was evaporated to dryness and purified by ion exchange chromatography using a DEAE-Sephadex (NH$_4$.CO$_3$ form) to give 120 mg of pure product after lyophilization and drying at 100° C. (15 hr); [α]$_D^{23}$+9.8° (1.1 H$_2$O). Thin layer chromatography on SiGF showed a single product spot that lined up with racemic product using acetonitrile (0.1N NH$_4$Cl) (7:3) UV $\lambda_{max}$ pH 7, 252, 275 shoulder.

EXAMPLE 6

The compounds prepared in Examples 1 and 2 were evaluated in vitro as antiviral agents against human cytomegalovirus.

One herpes virus strain employed was Strain McCrae of type 1 herpes (thymidine kinase positive virus) (HSV-1TK$^+$). This strain was prepared and titered in MA-104 cells and frozen at –90° C. until use. Also used were strain HF (HSV-1TK$^-$), strain E194 (HSV-2), NJB strain (MCMV), and strain AD169 (HCMV).

Continuous passaged MRC-5 cells obtained from the American Type Culture Collection (Bethesda, Md.) were used for testing of herpes-type virus, with growth medium consisting of Minimum Essential Medium (MEM) supplemented with 0.1% NaHCO$_3$ and 50 μL gentamicin.

To a 96 well microtiter plate containing an established 24 hour monolayer of cells from which the medium has been decanted was added 0.1 mL of varying (one-half log$_{10}$) concentrations of test compound, which incubated on the cell 15 minutes, after which 0.1 mL of virus in a concentration of 320 cell culture 50% infectious doses (CCID$_{50}$)/ 0.1 mL was added. The plate was covered with plastic wrap and incubated at 37° C. The cells were examined microscopically after 72 hours for evidence of cytotoxicity and for viral cytopathic effect (CPE). Results are set forth in Table 1:

TABLE 1

| Compound | Therapeutic Index* |
| --- | --- |
| 1-9 | 27.3 |
| 2-9 | >750 |
| 1-9/2-9 racemate | 750 |

*CD50 + ED50 (maximum efficacy seen in the case of multiple experiments).

As the racemate is believed to be an approximately 50:50 (w/w) mixture of the two enantiomers 1-9 and 2-9, it may be concluded that the majority of the antiviral activity of the racemate is due to the (R) enantiomer 2-9.

We claim:

1. A compound having the structural formula (VIIIb)

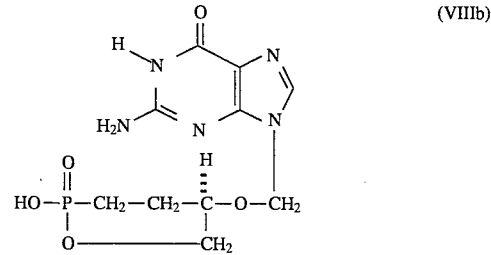

in enantiomerically pure form.

2. A pharmaceutical composition for treating herpes viral infection which comprises an effective amount of the compound of claim 1 in admixture with a pharmaceutically acceptable excipient.

3. A method to treat herpes viral infection in an infected subject, which comprises administering to the subject an effective amount of the compound of claim 1 in admixture with a pharmaceutically acceptable excipient.

* * * * *